(12) United States Patent
Voth et al.

(10) Patent No.: US 7,957,784 B2
(45) Date of Patent: Jun. 7, 2011

(54) BODY SURFACE MAPPING SYSTEM

(75) Inventors: Eric Jon Voth, Maplewood, MN (US); Don Curtis Deno, Andover, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1194 days.

(21) Appl. No.: 11/647,305

(22) Filed: Dec. 29, 2006

(65) Prior Publication Data

US 2008/0161671 A1    Jul. 3, 2008

(51) Int. Cl.
*A61B 5/04* (2006.01)

(52) U.S. Cl. ......... 600/388; 600/389; 600/393; 600/509

(58) Field of Classification Search .................. 600/374, 600/386, 388–390, 393, 509
See application file for complete search history.

(56) References Cited

U.S. PATENT DOCUMENTS

| | | | |
|---|---|---|---|
| 5,297,549 A | 3/1994 | Beatty et al. | |
| 5,553,611 A | 9/1996 | Budd et al. | |
| 5,662,108 A | 9/1997 | Budd et al. | |
| 5,697,377 A * | 12/1997 | Wittkampf | 600/374 |
| 5,983,126 A * | 11/1999 | Wittkampf | 600/509 |
| 6,640,119 B1 | 10/2003 | Budd et al. | |
| 6,728,562 B1 | 4/2004 | Budd et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |

* cited by examiner

*Primary Examiner* — Lee S Cohen
(74) *Attorney, Agent, or Firm* — Wiley Rein LLP

(57) ABSTRACT

A body-surface mapping system is disclosed that uses a plurality of electrodes to map at least a portion of a human torso without having to adjust the positions of the electrodes. The body-surface mapping system energizes groupings or regions of electrodes, then compares and adjusts the current driven through each grouping or region of electrodes to produce near-uniform fields. The electrodes of the body-surface mapping system may be interconnected by wires capable of sensing interelectrode distances, such that the system can reconstruct a detailed model of a patient's torso surface. The body-surface mapping system may also use a catheter in addition to the body surface electrodes to compute both endocardial and epicardial voltage distributions.

27 Claims, 3 Drawing Sheets

BODY SURFACE MAPPING SYSTEM

CROSS-REFERENCE TO RELATED APPLICATIONS

This application is related to U.S. application Ser. No. 11/618,676, filed 29 Dec. 2006, which is hereby expressly incorporated by reference as though fully set forth herein.

BACKGROUND OF THE INVENTION a. Field of the Invention

The instant invention relates to body-surface mapping of at least a portion of a human torso, and more particularly to methods and systems for noninvasive electrophysiology study. In particular, the instant invention relates to a garment or vest comprising a plurality of electrodes that are preferably interconnected. The garment or vest may by used alone or in combination with a catheter or probe to calculate endocardial and epicardial voltages to map and/or treat the human heart.

b. Background Art

Imaging and diagnosing cardiac electrical activity can be problematic because the electrical activity is time dependent and spatially distributed throughout the myocardium. Electrocardiographic techniques that include, for example, electrocardiograms (ECG) and vectorcardiography (VCG) can be limited in their ability to provide information and/or data on regional electrocardiac activity. These methods can also fail to localize bioelectric events in the heart.

Simultaneous recordings of potentials at tens or hundreds of locations on the torso, for example, is known and can provide body surface potential maps (BSPMs) over the torso surface. Although the BSPMs can indicate regional cardiac electrical activity in a manner that may be different from conventional ECG techniques, the known BSPM techniques, on their own, may provide a comparatively low resolution, smoothed projection of cardiac electrical activity that does not facilitate visual detection or identification of cardiac event locations (e.g., sites of initiation of cardiac arrhythmias) and details of regional activity (e.g., number and location of arrythmogenic foci in the heart).

It is also common to measure the electrical potentials present on the interior surface of the heart as a part of an electrophysiological study of a patient's heart. Typically such measurements are used to form a two-dimensional map of the electrical activity of the heart muscle. An electrophysiologist will use the map, for example to locate centers of ectopic electrical activity occurring within the cardiac tissues. One traditional mapping technique involves a sequence of electrical measurements taken from mobile electrodes inserted into the heart chamber and placed in contact with the surface of the heart. An alternative mapping technique takes essentially simultaneous measurements from a floating electrode array to generate a two-dimensional map of electrical potentials.

The two-dimensional maps of the electrical potentials at the endocardial surface generated by these traditional processes may be less than ideal. Traditional systems have been limited in resolution by the number of electrodes used. The number of electrodes dictated the number of points for which the electrical activity of the endocardial surface could be mapped. Therefore, progress in endocardial mapping has involved either the introduction of progressively more electrodes on the mapping catheter or improved flexibility for moving a small mapping probe with electrodes from place to place on the endocardial surface. Direct contact with electrically active tissue is required by most systems in the prior art in order to obtain well conditioned electrical signals.

With an increasing use of nonpharmacological anti-arrhythmic interventions (e.g., ablation), comparatively rapid and accurate localization of electrocardiac events—both endocardial and body-surface—can be beneficial.

BRIEF SUMMARY OF THE INVENTION

It is desirable to improve currently known systems for electrophysiology study. The present invention relates to such an improved system and methods of its use. More specifically, the present invention contemplates a system for body-surface mapping of electrical potentials of at least a portion of a human body, using a plurality of electrodes. The mapping system may comprise a flexible garment (e.g., a vest, large patch, or other structure) adapted to fit at least a portion of the human body, the flexible garment supporting a plurality of electrodes. A portion of the plurality of electrodes may be arranged in a plurality of regions. The mapping system may further have a localization system to determine relative distances between at least two regions of electrodes and an electronic device with a software program adapted to measure, and in some embodiments also to control, the drive currents for at least two regions of electrodes and to measure the linearities, and in some embodiments also the homogeneities, of the electrical fields created by those at least two regions. In such a mapping system of the present invention, the software program may compare the various regions of electrodes and identify at least one region that creates an electrical field that is more linear than, and in some embodiments also more homogeneous than, an electrical field generated by another region. A memory coupled to the electronic device could store information regarding the identified region or regions of most linear and/or most homogeneous electrodes, with the stored information comprising the drive currents for that region, and, in some embodiments, an identification of the electrodes within that region. Such a system could permit creation of near-uniform fields and allow for improved body-surface mapping of a portion of the human torso.

A plurality or all of the electrodes in the garment of the inventive mapping system may further be interconnected. These electrodes may be interconnected by piezoelectric wires such that relative distances between a plurality of the electrodes may be determined using information about stress forces that are applied to the plurality of piezoelectric wires. Further, the localization system of the present invention may comprise a device that can determine position information for some or each of the plurality of electrodes. The position information could comprise interelectrode spacings, such that three dimensional positions of some or each of the plurality of electrodes may be calculated.

The garment of the novel mapping system may further have a plurality of electrodes arranged in a plurality of rows, where the rows may be placed about the circumference of the human body. The garment may further have a plurality of spacers designed to locate at least one of the plurality of rows at fixed distances from adjacent rows, wherein the lengths of the plurality of spacers would be known to the mapping system. Some or each of the plurality of rows may further be adjustable such that a circumference measurement for each row of electrodes may be determined by the system. Such a system of the present invention may further have an adjustable member coupled to the system such that the circumference measurement could be measured automatically by the mapping system. Such an embodiment of the body-surface mapping system of the present invention could provide even more accurate measurements of body-surface potential for each patient.

The mapping system of the present invention may further comprise one or more catheters or probes adapted to move throughout the heart or a heart chamber. The electronic device of the system may then be capable of collecting data from both the plurality of electrodes and the catheters or probes to collect, e.g., both body-surface potentials and intracardiac voltages.

A different embodiment of the body-surface mapping system of the present invention may have a flexible vest adapted to fit at least a portion of the human torso, the flexible vest having a plurality of electrodes. The mapping system may also have a localization system to determine relative distances between a plurality of pairs of the plurality of electrodes and an electronic device capable of electronically connecting to the flexible vest. The electronic device may have a processor to determine optimal drive currents for the plurality of electrodes to create a homogeneous and linear electrical field in which a position of a sensor located within an interior of the human torso can be determined with respect to at least two orthogonal axes. This mapping system would further have a software program, which may provide position information of the sensor within the human torso.

The flexible vest of the novel system may further have at least 128 electrodes and at least two of the electrodes may be interconnected by piezoelectric or mechanical wires. This mapping system may further have a balloon catheter, which may be a multi-electrode balloon catheter, for insertion into the human body. The software program of the system may then be adapted to electronically connect to the balloon catheter and further adapted to compute both epicardial and endocardial voltage distributions from measurements made by the balloon catheter and/or a plurality of the electrodes. The software program may further be adapted to measure voltages relative to at least the balloon catheter.

The flexible vest may further have a plurality of electrodes arranged in a plurality of rows, wherein the plurality of rows may be placed about a circumference of the human body. This vest could then further have a plurality of spacers designed to locate at least one of the plurality of rows at fixed distances from adjacent rows, wherein the lengths of the spacers would be known to the mapping system. The plurality of rows may further be adjustable such that a circumference measurement for each row of electrodes of the plurality of rows may be determined by the system. The plurality of rows of electrodes may further include an adjustable member coupled to the system such that the circumference measurement could be measured automatically by the system.

In another aspect, the present invention may be a device capable of determining the torso geometry of a human. Such a device may have a plurality of electrodes arranged in a plurality of rows, wherein the plurality of rows may be placed about a circumference of a portion of the human. The plurality of electrodes may be supported or encompassed by a semi-rigid, flexible material. The device may further have an electronic device capable of electronically connecting to the plurality of electrodes. In such an embodiment, at least one of the plurality of rows of electrodes may be arranged to form a circumferential row of electrodes having a closure member at at least one end. The closure member could have an electrical contact such that when the closure member is used to secure the device to a human, the closure member is capable of registering information regarding a closing position. The electronic device could then comprise software adapted to compute a torso model of the human based on the closing position of the closure member. The closure member may be a snap fastened along a side of the device that is opposite a side of the device that would be placed near a heart of a human patient upon whom the device is placed. Each electrode of the inventive device may be further connected to at least one other electrode by mechanical wires such that the electrodes are interconnected.

The present invention further relates to a method for measuring or determining epicardial and endocardial voltages and/or potentials in a human. According to such a method, a device having a plurality of electrodes may be applied to a portion of the torso of a human to measure body-surface potentials. A catheter such as a balloon catheter or mapping catheter may also be directed into the cardiac region of the human patient to measure an intracardiac voltage. Software may then be used to collect the body-surface potentials and intracardiac voltages and to concurrently reconstruct epicardial and endocardial voltage distributions. The electrodes in the device used in such a method may be interconnected by piezoelectric wires such that relative distances between a plurality of the electrodes may be determined using information about stress forces that are applied to the plurality of piezoelectric wires. The plurality of electrodes of the device may further be arranged in a plurality of regions of electrodes such that at least two of the regions of electrodes may each be energized with a different current such that measurement of the epicardial voltage distribution can be made in a plurality of regions without adjusting the position of the plurality of electrodes. In such a method, the software may be adapted to control and measure the drive currents for at least two regions of electrodes and to measure the homogeneity and linearity of an electrical field created by the at least two regions, such that the software may compare the relative linearities for a plurality of regions of electrodes and identify and control a region of electrodes that creates an electrical field that is more linear than an electric field generated by at least one other region.

The foregoing and other aspects, features, details, utilities, and advantages of the present invention will be apparent from reading the following description and claims, and from reviewing the accompanying drawings.

DETAILED DESCRIPTION OF THE INVENTION

The present invention generally relates to a system or device useful for body-surface mapping, myocardial activation pattern mapping, or determining the torso geometry of a human. In various preferred embodiments, the system or device has a plurality of electrodes divided into regions or groupings of electrodes such that different regions or groupings may be energized. The regions or groupings of electrodes need not be physically segregated. Indeed, in several preferred embodiments, the regions or groupings of electrodes are variable, such that, for example, in a device with 128 electrodes, there may be as many as sixty-four regions or groups of electrodes, or as few as two regions or groups of electrodes, and the regions or groups may comprise as few as two or as many as 126 neighboring or adjacent electrodes.

In some preferred embodiments, a software program measures the drive currents for at least two regions of electrodes and measures the linearity of an electrical field created by those regions (that is, it measures the linearity of each electric field created by each of the at least two regions of electrodes). The software program may also be adapted to control the drive currents for at least two regions of electrodes. In addition to measuring the linearity of the electrical fields, the software program may also measure the homogeneity of the electrical fields. The software program can then compare the various regions of electrodes and identify at least one region that creates an electrical field that is more linear, and, in some embodiments, more homogeneous, than an electrical field generated by another region. The software program could also be adapted to mate different electrodes to find an electrode pairing that provides a more linear or more homogeneous field than that generated by another electrode pairing. These preferred embodiments allow for the creation of precise and near-uniform fields, thereby allowing for more accurate and improved body-surface mapping of a portion of the human torso, particularly the cardiac area. Specifically, near-uniform fields may be created based on using a patient-specific torso model or morphing a representative solution onto a patient's surface geometry. In one preferred embodiment, the system or device employs a roving catheter or probe to send electrical feedback as the catheter or probe is moved to various positions in the heart while different source current distributions are applied to the body-surface electrodes.

Figure 1:
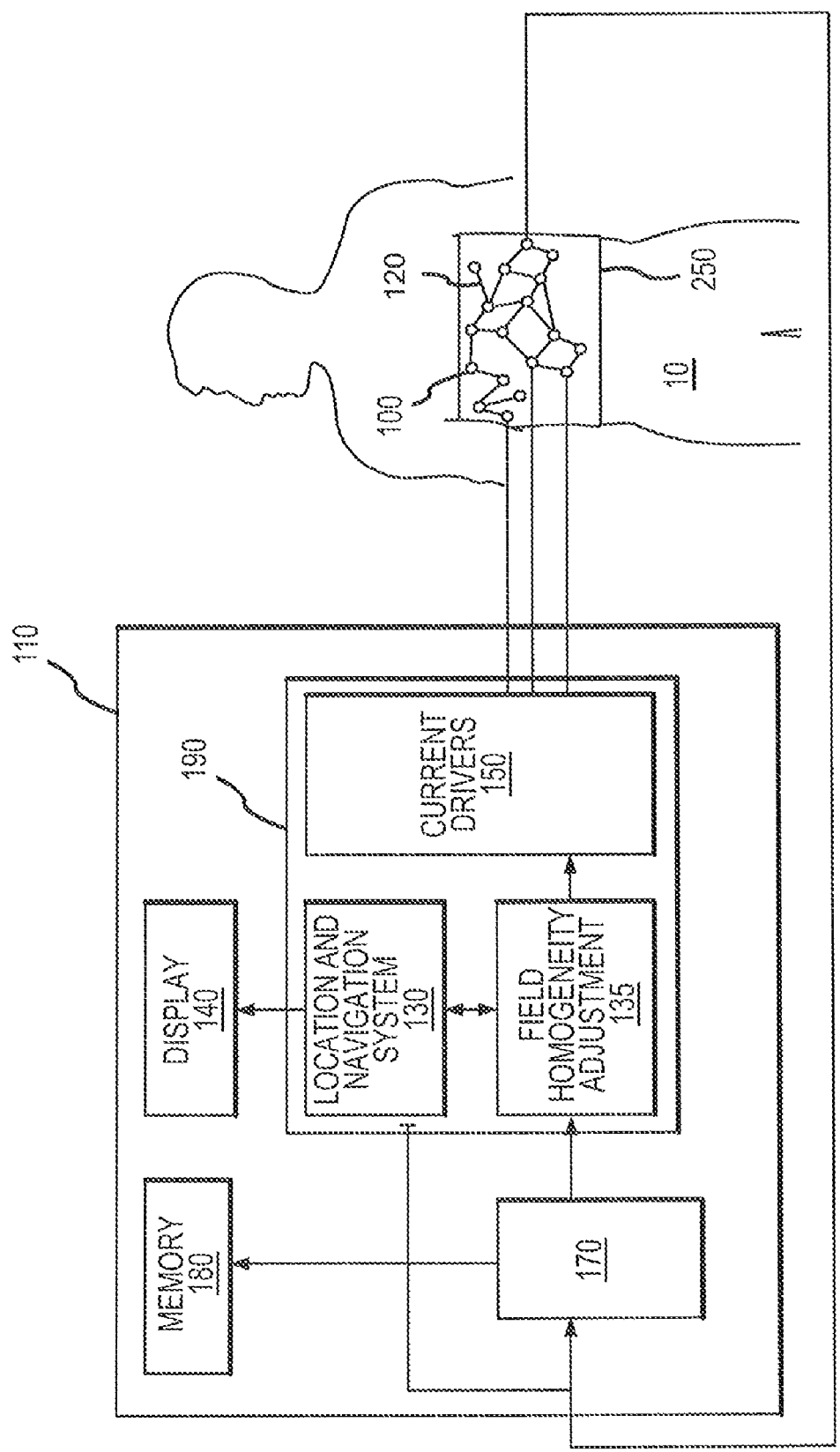
FIG. 1 is a block diagram showing one embodiment of a body-surface mapping system of the present invention, having a plurality of interconnected electrodes connected to a computer system comprising a localization system.

FIG. 1 demonstrates a body-surface mapping system according to some of the preferred embodiments of the present invention. As shown, a plurality of electrodes 100 are located on a human torso 10. The electrodes may be supported by a garment 250, such as a vest 300 (shown in FIG. 3), a large patch, an elastic belt, or the like. The body-surface mapping system may have any number of electrodes. In a preferred embodiment, the body-surface mapping system has at least 64 electrodes. In a further preferred embodiment, the body-surface mapping system has at least 128 electrodes. In yet another preferred embodiment, the body-surface mapping system has at least 256 electrodes.

The electrodes 100 are connected to navigation field current drivers 150 that are part of a localization system 190 that also comprises a location and navigation system 130 and a field homogeneity adjustment 135. The localization system 190 is coupled to an electronic device with a software program 170 or multiple software programs. The localization system 190 and software program 170 may all be housed within the same computer system 110, as shown, and may run using a related family of algorithms, or may be resident on different computer systems. The electrodes 100 may be energized by the current drivers 150 in different groupings or regions of electrodes. The location and navigation system 130 then measures the relative distances between at least two regions or groupings of electrodes while the software program 170 measures the drive currents for the energized regions of electrodes. The homogeneity and linearity of an electrical field created by the various regions or groupings of electrodes is thereby measured. The software program 170 then compares the relative linearities, and in some embodiments the relative homogeneities, of the electrical fields created by the various regions or groupings of electrodes and identifies at least one region or grouping that creates an electrical field that is more linear and/or homogeneous than an electrical field generated by another region. The software program 170 and the location and navigation system 130 also send information to the field homogeneity adjustment 135 that can communicate with the current drivers 150 to energize a different grouping or region of electrodes. The software program could also be adapted to mate different electrodes to find an electrode pairing that provides a more linear or more homogeneous field than that generated by another electrode pairing. As a result, a more homogeneous electric field is established for navigation and mapping with improved accuracy. The computer system 110 of FIG. 1 further has a memory 180 to store information regarding the identified region or regions of electrodes of most linear and/or homogeneous fields, including the drive currents for that region or regions. The memory 180 may be part of the computer system 110 or may be coupled to the computer system 110. In some embodiments, the resulting data can be viewed on a display 140, which may also be coupled to or part of the computer system 110.

As further shown in FIG. 1, in some preferred embodiments, at least a portion of the plurality of electrodes 100 is interconnected. The electrodes 100 may be interconnected by piezoelectric wires 120 or mechanical wires able to determine the distance between many or at least a pair of neighboring electrodes 100. The piezoelectric wires 120 use stress forces applied to the wires to determine relative distances between the interconnected electrodes. This electrode spacing information can be used by the location and navigation system 130 and/or by the software program 170 to further optimize field uniformity.

Figure 2:
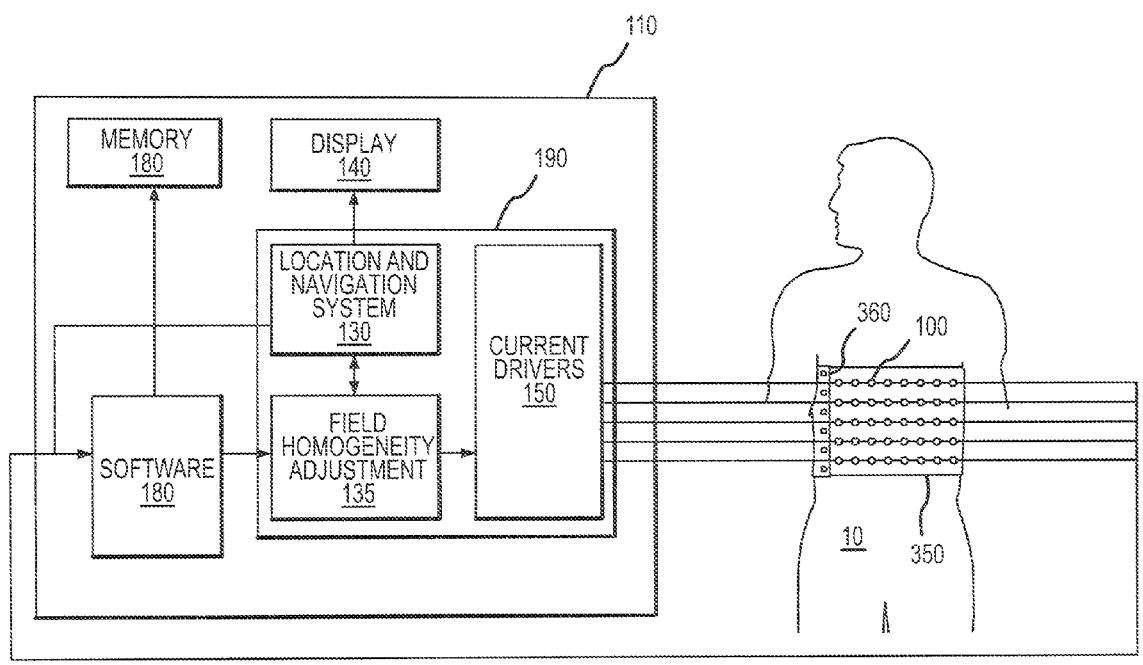
FIG. 2 is a block diagram showing another embodiment of a body-surface mapping system of the present invention, having a plurality of electrodes supported in a semirigid, flexible garment with a closure member along one side.

In another embodiment of the present invention, as shown in FIG. 2, a plurality of electrodes 100 is supported or encompassed by a semirigid, flexible material 350. In this embodiment, the electrodes 100 may be arranged in a plurality of rows. The semirigid material stretches only in circumference along each row of electrodes. The semirigid material has a closure member 360 at one end. The closure member may have several straps or snaps that have an electrical contact such that when the closure member is used to secure the device to a human, the snaps or straps register the position in which they are closed. This position information is then communicated to the location and navigation system 130 and/or a software program 180 (which may be the same or different from the software program 170 of FIG. 1). The software program 180 then computes a patient-specific torso model based on the patient's torso circumference at each row of electrodes. The semirigid, flexible material may be in the shape of a vest or other suitable garment. In order to accommodate a wide variety of human torso sizes, such a vest or other suitable garment may come in a variety of sizes.

The geometry and conductivity information collected by the systems of the present invention, as shown in FIGS. 1 and 2, may be used to reconstruct epicardial potentials, by using the plurality of electrodes as passive sensors of the fields created by myocardial activation. For example, by measuring torso potentials at each electrode position, a boundary element algorithm (similar to, e.g., the Ensite™ algorithm) could estimate potentials everywhere on the epicardium. The potentials could be displayed in real time or saved in memory and viewed in a review mode to aid in clinical diagnosis.

Figure 3:
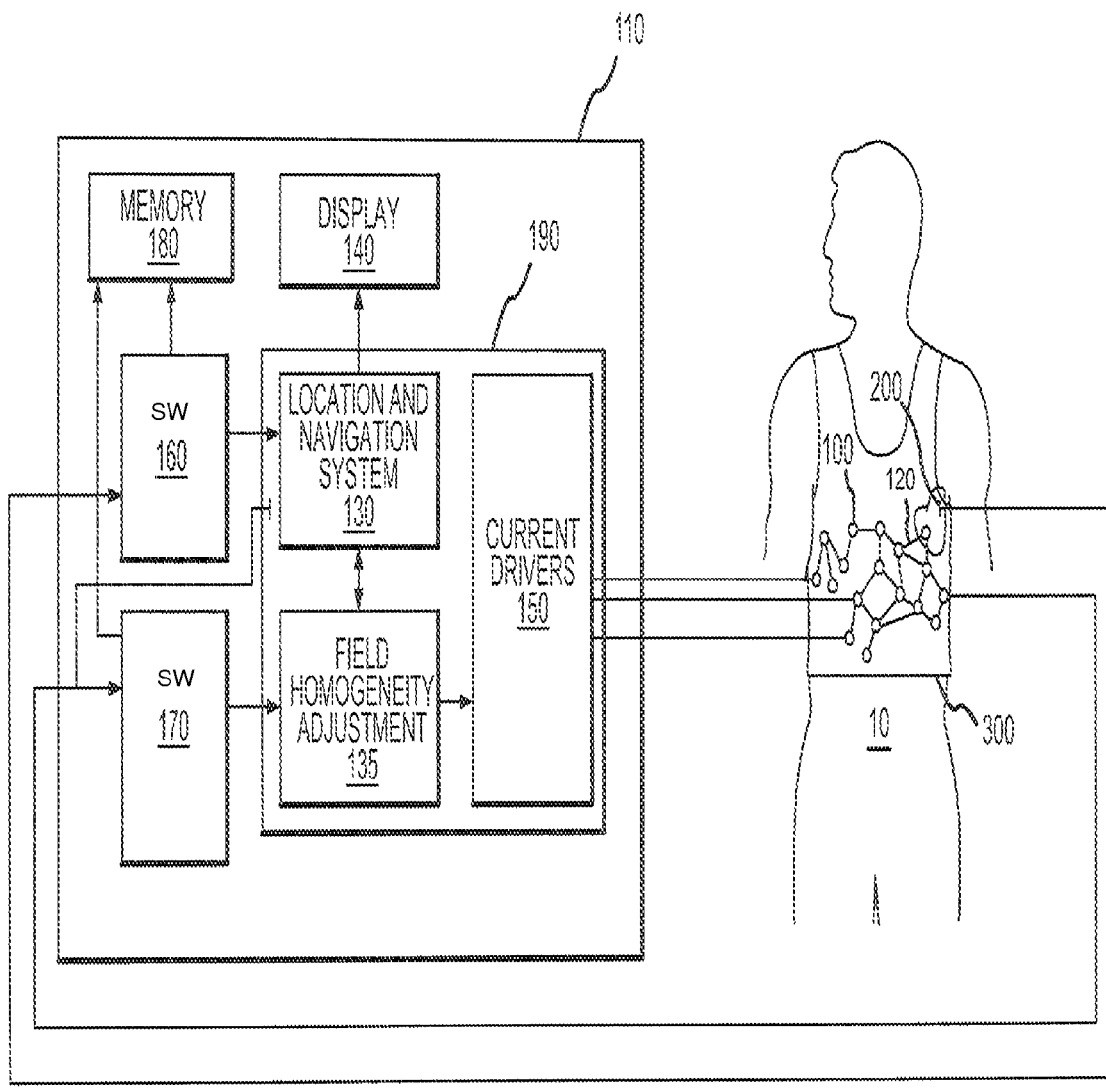
FIG. 3 is a block diagram showing another embodiment of a body-surface mapping system of the present invention, having a vest with a plurality of electrodes and a catheter both connected to a computer system for computing both endocardial and epicardial voltages.

In some embodiments of the present invention, as shown in FIG. 3, the body-mapping surface system further comprises a catheter 200. The catheter may be a mapping catheter, a sensor probe, or a multi-electrode catheter such as the Ensite™ balloon catheter. The mapping catheter 200 is also linked to a software program 160. As shown, the software program 160 is part of computer system 110 but is a different program than software program 170. In some preferred embodiments, the software programs 160 and 170 are part of the same software program. In other preferred embodiments, the software programs are resident on separate computer systems. The localization and mapping systems described in the following patents, which are all incorporated herein by reference in their entireties, can be used with the present invention: U.S. Pat. Nos. 6,990,370, 6,978,168, 6,947,785, 6,939,309, 6,728,562, 6,640,119. The use of other localization and mapping systems is also contemplated. Using the catheter 200 in conjunction with the plurality of body-surface mapping electrodes 100, the system of the present invention shown in FIG. 3 is able to measure both body-surface potentials and intracardiac voltages to compute both endocardial and epicardial voltages.

Some preferred embodiments of the present invention, for example the embodiment depicted in FIG. 3, may be used in a method to compute endocardial and epicardial voltages from a human patient. A vest 300 having a plurality of electrodes 100 may be applied to a portion of the torso of a human 10 to measure body-surface potentials. A catheter 200 such as a balloon catheter or mapping catheter may also be directed into the cardiac region of the human patient to measure an intracardiac voltage. Software programs 160 and 170 may then be used to collect the body-surface potentials and intracardiac voltages and to concurrently reconstruct epicardial and endocardial voltage distributions. The electrodes 100 in the device used in such a method may be interconnected by piezoelectric wires 120 such that relative distances between a plurality of the electrodes may be determined using information about stress forces that are applied to the plurality of piezoelectric wires 120. The plurality of electrodes 100 of the vest may further be arranged in a plurality of regions of electrodes such that at least two of the regions of electrodes may each be energized with a different current such that measurement of the epicardial voltage distribution can be made without adjusting the position of the plurality of electrodes 100. In such a method, the software may be adapted to control and measure the drive currents for at least two regions of electrodes and to measure the homogeneity and linearity of an electrical field created by the at least two regions, such that the software may identify a region of electrodes that creates an electrical field that is more homogeneous and linear than an electric field generated by at least one other region.

Although only a few embodiments of this invention have been described above with a certain degree of particularity, those skilled in the art could make numerous alterations to the disclosed embodiments without departing from the spirit or scope of this invention. In addition, the body-surface mapping system of the present invention may be utilized to drive enough current through regions or groupings of electrodes to estimate the conductivity of a variety of tissues within the human torso, such as lung, blood, bone, and muscle, and may also be capable of determining the relative positions, conductivities, and sizes of such tissue.

All directional references (e.g., upper, lower, upward, downward, left, right) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A system for body-surface mapping of electrical potentials of at least a portion of a human body, the system comprising:
    a) a flexible garment adapted to fit at least a portion of the human body, said flexible garment comprising a plurality of interconnected electrodes wherein at least a portion of the plurality of electrodes are arranged in a plurality of regions of electrodes;
    b) an electronic device having a software program adapted to measure drive currents for at least two regions of electrodes and to measure linearities of at least two electrical fields created by the at least two regions of electrodes, such that the program may compare the at least two regions of electrodes and identify at least one region that creates an electrical field that is more linear than an electrical field generated by at least one other region; and
    c) a memory coupled to said electronic device for storing information regarding at least the identified at least one region of electrodes, said stored information comprising the drive currents for the at least one region.

2. The system of claim 1 wherein said software program is further adapted to measure homogeneities of the at least two electrical fields created by the at least two regions of electrodes, such that the program may identify at least one region that creates an electrical field that is more homogeneous than an electric field generated by at least one other region.

3. The system of claim 1 wherein said software program is further adapted to control drive currents for the at least two regions of electrodes.

4. The system of claim 1 wherein the plurality of interconnected electrodes are interconnected by piezoelectric wires such that relative distances between electrodes within the plurality of interconnected electrodes may be determined using information about stress forces that are applied to the plurality of piezoelectric wires.

5. The system of claim 1 further comprising a localization system to determine relative distances between at least two regions of electrodes.

6. The system of claim 5 wherein the localization system comprises a device that can determine position information for each of the plurality of interconnected electrodes, said position information comprising interelectrode spacings, such that three dimensional positions of each of the plurality of interconnected electrodes may be calculated.

7. The system of claim 1 wherein the garment comprises:
    a plurality of electrodes arranged in a plurality of rows, wherein the plurality of rows may be placed about a circumference of the human body; and
    a plurality of spacers designed to locate at least one of said plurality of rows at fixed distances from adjacent rows; wherein the lengths of said plurality of spacers is known to the system.

8. The system of claim 7 wherein each of said plurality of rows is adjustable such that a circumference measurement for each row of electrodes of the plurality of rows may be determined by the system.

9. The system of claim 8 wherein each of said plurality of rows includes an adjustable member coupled to the system such that the circumference measurement is measured automatically by the system.

10. The system of claim 1 further comprising a catheter adapted to move throughout a heart chamber, wherein the electronic device is capable of collecting data from both the plurality of interconnected electrodes and the catheter.

11. A system for body-surface mapping of electrical potentials of at least a portion of a human torso, the system comprising:
   a) a flexible vest adapted to fit at least a portion of the human torso, said flexible vest comprising a plurality of electrodes;
   b) a localization system to determine relative distances between a plurality of pairs of said plurality of electrodes; and
   c) an electronic device capable of electronically connecting to said flexible vest, said electronic device comprising a processor to drive currents for said plurality of electrodes to create an electrical field in which a position of a sensor located within an interior of the human torso can be determined with respect to at least two orthogonal axes.

12. The system of claim 11 wherein at least two of the plurality of electrodes are interconnected by piezoelectric wires or mechanical wires.

13. The system of claim 12 wherein said flexible vest comprises at least 128 electrodes.

14. The system of claim 13 further comprising a balloon catheter and a software program, wherein the software program is adapted to electronically connect to said balloon catheter and wherein the software program is adapted to compute both epicardial and endocardial voltage distributions from measurements made by the balloon catheter, a plurality of said plurality of electrodes, or a combination thereof, and is further adapted to measuring voltages relative to at least said balloon catheter.

15. The system of claim 14 wherein the vest comprises:
   a plurality of electrodes arranged in a plurality of rows, wherein the plurality of rows may be placed about a circumference of the human body; and
   a plurality of spacers designed to locate at least one of said plurality of rows at fixed distances from adjacent rows; wherein the lengths of said plurality of spacers is known to the system.

16. The system of claim 15 wherein each of said plurality of rows is adjustable such that a circumference measurement for each row of electrodes of the plurality of rows may be determined by the system.

17. The system of claim 16 wherein each of said plurality of rows includes an adjustable member coupled to the system such that the circumference measurement is measured automatically by the system.

18. A method for measuring epicardial and endocardial voltages in a human, said method comprising the steps of:
   a) applying a device to a portion of the torso of the human to measure body-surface potentials, the device comprising a plurality of electrodes;
   b) directing a balloon catheter into the cardiac region of the human patient to measure an intracardiac voltage; and
   c) using software to collect the body-surface potentials and intracardiac voltages and to concurrently reconstruct epicardial and endocardial voltage distributions.

19. The method of claim 18 wherein the plurality of electrodes are interconnected by piezoelectric wires such that relative distances between a plurality of the electrodes may be determined using information about stress forces that are applied to the plurality of piezoelectric wires.

20. The method of claim 18 wherein at least a portion of the plurality of electrodes are arranged in a plurality of regions of electrodes, the method further comprising the step of energizing at least two of said regions of electrodes each with a different current such that measurement of the epicardial voltage distribution can be made in a plurality of regions of electrodes without adjusting the position of the plurality of electrodes.

21. The method of claim 20 wherein the software is adapted to measure the drive currents for at least two regions of the plurality of regions of electrodes and to measure the linearity of an electrical field created by said at least two regions, such that the software may compare the relative linearities for a plurality of regions of electrodes and identify a region of electrodes that creates an electrical field that is more linear than an electric field generated by at least one other region of electrodes.

22. A device capable of determining torso geometry of a human, the device comprising:
   a) a plurality of electrodes arranged in a plurality of rows, wherein the plurality of rows may be placed about a circumference of a portion of the human;
   b) a semirigid, flexible material encompassing the plurality of electrodes; and
   c) an electronic device capable of electronically connecting to said plurality of electrodes;
   wherein at least one of the plurality of rows of electrodes is circumferentially arranged to form a circumferential row of electrodes and wherein the circumferential row has a closure member at an end of thereof; said closure member having an electrical contact such that when said closure member is used to secure the device to the human, the closure member is capable of registering information regarding a closing position and wherein the electronic device comprises software adapted to computing a torso model of the human based on the closing position of said closure member.

23. The device of claim 22 wherein the closure member is a snap fastened along a side of the device that is opposite a side of the device that would be placed near a heart of a human patient upon whom the device is placed.

24. The device of claim 23 wherein the device comprises a vest.

25. The device of claim 22 wherein each electrode of the plurality of electrodes is connected to at least one other electrode of the plurality of electrodes by mechanical wires to make interconnected electrodes.

26. The device of claim 22 having a plurality of groupings of electrodes to form regions of electrodes wherein each said region of electrodes is capable of being energized by a different current.

27. A system for body-surface mapping of electrical potentials of at least a portion of a human torso, the system comprising:
   a) a flexible garment adapted to fit at least a portion of the human torso, said flexible garment comprising a plurality of electrodes arranged to form a plurality of regions of electrodes; and
   b) an electronic device capable of electronically connecting to said flexible garment, said electronic device comprising a processor to determine optimal drive currents for said plurality of electrodes and to take resulting measurements, said electronic device further capable of energizing said plurality of regions of electrodes each with a different current such that measurements can be made without adjusting the position of the plurality of electrodes.

* * * * *